US009487818B2

(12) United States Patent
Kumaravel et al.

(10) Patent No.: US 9,487,818 B2
(45) Date of Patent: Nov. 8, 2016

(54) TOP2A INHIBITION BY TEMOZOLOMIDE AND ITS PREDICTIVE VALUE OF GBM PATIENTS SURVIVAL

(75) Inventors: Somasundaram Kumaravel, Bangalore (IN); Arivazhagan Arimappamagan, Bangalore (IN); Kandavel Thennarasu, Bangalore (IN); Alangar Sathyaranjandas Hegde, Bangalore (IN); Ashwathnarayana Chandramouli, Bangalore (IN); Santosh Vani, Bangalore (IN); Paturu Kondaiah, Bangalore (IN); Satyanarayana Rao Manchanahalli Rangaswamy, Bangalore (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 13/825,750

(22) PCT Filed: Sep. 22, 2011

(86) PCT No.: PCT/IB2011/002205
§ 371 (c)(1),
(2), (4) Date: Jul. 10, 2013

(87) PCT Pub. No.: WO2012/038812
PCT Pub. Date: Mar. 29, 2012

(65) Prior Publication Data
US 2013/0280707 A1 Oct. 24, 2013

(30) Foreign Application Priority Data

Sep. 23, 2010 (IN) .......................... 2270/DEL/2010

(51) Int. Cl.
*C12Q 1/533* (2006.01)
*A61K 31/495* (2006.01)
*G01N 33/574* (2006.01)
(52) U.S. Cl.
CPC ............. *C12Q 1/533* (2013.01); *A61K 31/495* (2013.01); *G01N 33/57407* (2013.01); *C12Q 2600/158* (2013.01); *C12Q 2600/178* (2013.01); *G01N 2333/99* (2013.01); *G01N 2800/52* (2013.01)
(58) Field of Classification Search
USPC ........................................................ 435/6.11
See application file for complete search history.

(56) References Cited

U.S. PATENT DOCUMENTS

2003/0165954 A1\* 9/2003 Katagiri et al. ................... 435/6
2007/0037186 A1\* 2/2007 Jiang .................... C12Q 1/6886
435/6.12
2009/0269351 A1\* 10/2009 Phillips et al. ............. 424/139.1

OTHER PUBLICATIONS

Bredel M, Piribauer M, Marosi C, et al. High expression of DNA topoisomerase II-α and Ki-67 antigen is associated with prolonged survival in glioblastoma patients. Eur J Cancer. 2002. 38:1343-1347.\*
Kristyanto H, Utomo AR. Pharmacogenetic application in personalized cancer treatment. Acta Med Indones. Apr. 2010;42(2):109-15. Review.\*
Stupp R, European Organisation for Research and Treatment of Cancer Brain Tumour and Radiation Oncology Groups, Effects of radiotherapy with concomitant and adjuvant temozolomide versus radiotherapy alone on survival in glioblastoma in a randomised phase III study: 5-year analysis of EORTC-NCIC trial. Lancet Oncol. May 2009; 10(5): 459-66.\*
Enard W, Khaitovich P, Klose J, Zöllner S, Heissig F, Giavalisco P, Nieselt-Struwe K, Muchmore E, Varki A, Ravid R, Doxiadis GM, Bontrop RE, Pääbo S. Intra- and interspecific variation in primate gene expression patterns. Science. Apr. 12, 2002; 296(5566):340-3.\*
Whitehead A, Crawford DL. Variation in tissue-specific gene expression among natural populations. Genome Biol. 2005; 6(2):R13. Epub Jan. 26, 2005.\*
Arivazhagan et al. Higher topoisomerase 2 alpha gene transcript levels predict better prognosis in GBM patients receiving temozolomide chemotherapy: identification of temozolomide as a TOP2A inhibitor. J Neurooncol. Apr. 2012;107(2):289-97. Epub Nov. 19, 2011.\*
Dingemans AM, Witlox MA, Stallaert RA, van der Valk P, Postmus PE, Giaccone G. Expression of DNA topoisomerase IIalpha and topoisomerase IIbeta genes predicts survival and response to chemotherapy in patients with small cell lung cancer. Clin Cancer Res. Aug. 1999;5 (8):2048-58.\*

(Continued)

*Primary Examiner* — Gary Benzion
*Assistant Examiner* — Olayinka Oyeyemi
(74) *Attorney, Agent, or Firm* — Banner & Witcoff, Ltd.

(57) ABSTRACT

The present invention provides a TOP2A inhibition by temozolomide useful for predicting glioblastoma patient's survival. Glioblastoma (GBM) is the most common, malignant primary adult brain tumor. The conventional treatments for GBM, include surgery, radiation, and chemotherapy which have only modestly improved patient survival. The patients with GBM expressing higher TOP2A transcript levels had better prognosis. More interestingly, the present invention reports that temozolomide is an inhibitor of TOP2A activity in vitro. The present invention further shows that siRNA knock down of TOP2A rendered a glioma cell line resistant to temozolomide chemotherapy. Thus it is demonstrated for the first time that temozolomide is a TOP2A inhibitor and establishes that TOP2A transcript levels determines the chemosensitivity of glioblastoma to temozolomide therapy thus explaining the very high levels of TOP2A transcript being a good prognostic indicator in GBM patients receiving temozolomide chemotherapy.

3 Claims, 4 Drawing Sheets

(56) References Cited

OTHER PUBLICATIONS

Figure 1:
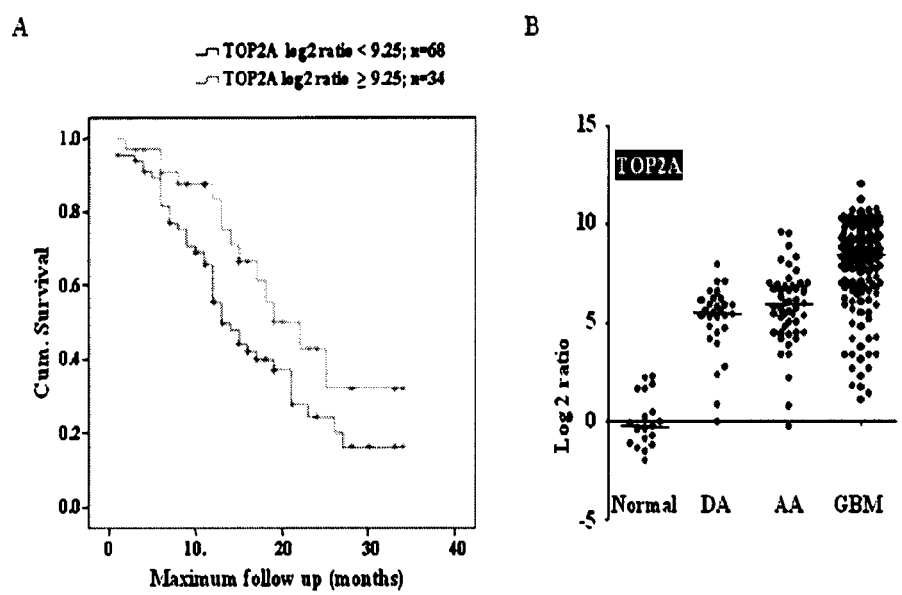

Grandgirard N, Ly-Sunnaram B, Ferrant D, Gandemer V, Edan C, Le Gall E, Moulinoux JP, Leray E, Goasguen JE. Impact of Topoisomerase II alpha and spermine on the clinical outcome of children with acute lymphoblastic leukemia. Leuk Res. May 2004;28(5):479-86.*

Schrader C, Meusers P, Brittinger G, Teymoortash A, Siebmann JU, Janssen D, Parwaresch R, Tiemann M. Topoisomerase IIalpha expression in mantle cell lymphoma: a marker of cell proliferation and a prognostic factor for clinical outcome. Leukemia. Jul. 2004; 18(7):1200-6.*

Reddy et al. (2008a). Novel glioblastoma markers with diagnostic and prognostic value identified through transcriptome analysis. Clin Cancer Res. May 15, 2008; 14(10):2978-87.*

Reddy et al. (2008b). PBEF1/NAmPRTase/Visfatin: a potential malignant astrocytoma/glioblastoma serum marker with prognostic value. Cancer Biol Ther. May 2008; 7(5):663-8.*

International Search Report mailed May 2, 2012 (PCT/IB2011/002205); ISA/US.

Kristyanto et al., Pharmacogenetic Application in Personalized Cancer Treatment, Pharmacogenetic Application in Personalized Cancer Treatment, Apr. 2010, vol. 42, No. 2; p. 112, col. 2, para. 3, p. 112, col. 2, para. 4, p. 113, col. 1, para. 1.

* cited by examiner

TOP2A INHIBITION BY TEMOZOLOMIDE AND ITS PREDICTIVE VALUE OF GBM PATIENTS SURVIVAL

CROSS REFERENCE TO RELATED APPLICATIONS

The present application is a U.S. National Phase filing of International Application No. PCT/IB2011/002205, filed on Sep. 22, 2011, designating the United States of America and claiming priority to Indian Patent Application No. 2270/DEL/2010, filed Sep. 23, 2010, and the present application claims priority to and the benefit of all the above-identified applications, which are incorporated by reference herein in their entireties.

FIELD OF THE INVENTION

The present invention relates to topoisomerase II alpha (TOP2A) inhibition by temozolomide useful for predicting glioblastoma patient's survival.

More particularly the present invention demonstrates that TOP2A transcript levels determines the chemosensitivity of glioblastoma to temozolomide therapy thus explaining the very high levels of TOP2A transcript being a good prognostic indicator in GBM patients receiving temozolomide chemotherapy.

BACKGROUND OF THE INVENTION

Glioblastoma, the grade IV astrocytoma, is the most malignant and most common primary adult brain cancer (Furnari et al., 2007). The highly heterogenous and infiltrative nature of these tumors makes complete resection virtually not possible and hence despite the postoperative treatment modalities, the median survival is very poor. While postoperative radiotherapy alone provided very small survival advantage, the addition of nitrosourea-based chemotherapy to radiotherapy gave modest benefit of increase in 1-year survival rate of 6%, such as from 40% to 46% and a 2-month increase in median survival time (Stewart, 2002). A 5-year analysis of the EORTC-NCIC trial showed addition of concomitant and cyclical adjuvant temozolomide, a DNA alkylating agent, to standard postoperative radiotherapy improved median survival and 2-year survival significantly relative to postoperative radiotherapy alone (Stupp et al., 2009). The overall survival rate was 27.2% at 2 years, 16.0% at 3 years, 12.1% at 4 years and 9.8% at 5 years with temozolomide versus 10.9%, 4.4%, 3.0%, and 1.9% respectively with radiotherapy alone (Stupp et al., 2009). In addition, the median survival increased to 14.6 months from 12.1 months (Stupp et al., 2009). More importantly, methylation of MGMT promoter was found to be the strongest predictor for outcome and benefit from temozolomide chemotherapy (Stupp et al., 2009). Analysis of progression-free survival showed an advantage only for patients whose tumor had a methylated MGMT promoter who were treated with temozolomide and radiotherapy.

These findings suggest the existence of specific gene signatures which will identify sub classes of patients with better response to temozolomide chemotherapy.

In the present invention a prospective study is carried out where patients were selected with standard inclusion/exclusion criteria and subjected to uniform treatment protocol, which included maximal safe resection of the tumor followed by radiotherapy with concomitant and cyclical adjuvant temozolomide therapy. The patients' survival data was correlated with tumor gene expression profile for identifying genes whose expression signature could predict survival. We report here our observations regarding influence of high topoisomerase II alpha (TOP2A) transcripts in GBM on patient survival. We further demonstrate by functional studies that temozolomide inhibits TOP2A activity in vitro and silencing of TOP2A in glioma cells rendered them temozolomide resistant. An assessment of TOP2A and other isoforms of topoisomerase across the grades of astrocytoma were also performed to elucidate their role in glioma.

OBJECTIVES OF THE INVENTION

The main object of the invention is to provide a prognostic marker, TOP2A, which is useful for predicting the type of chemotherapy treatment to be given to glioblastoma patients.

Another object of the invention is to provide a method of determining prognosis of glioblastoma in human subjects, wherein the said method comprises determining the level of expression of the gene TOP2A in a test sample of brain tumor tissue cells obtained from human subjects who underwent surgery and ready to receive radiotherapy with concomitant and cyclical adjuvant temozolomide therapy, and in a control sample of known normal brain tissue cells, wherein a higher level of expression of TOP2A in the test sample, as compared to the control sample, indicates good prognosis and better survival of glioblastoma in the human subject from which the test sample is obtained.

SUMMARY OF THE INVENTION

The present invention provides a prognostic marker and a method of determining prognosis of glioblastoma in human subjects, wherein the said method comprises determining the level of expression of the gene TOP2A in a test sample of brain tumor tissue cells obtained from human subjects who underwent surgery and ready to receive radiotherapy with concomitant and cyclical adjuvant temozolomide therapy, and in a control sample of known normal brain tissue cells, wherein a higher level of expression of TOP2A in the test sample, as compared to the control sample, indicates good prognosis and better survival of glioblastoma in the human subject.

DESCRIPTION OF FIGURES AND TABLES

FIG. 1

A) TOP2A expression and GBM patient survival.

Kaplan-Meier survival estimates for 102 GBM patients are calculated for TOP2A transcript levels. Survival curves for the groups positive (log 2 ratio≥9.25; n=34) and negative (log 2 ratio<9.25; n=68) for TOP2A in univariate analysis. The cases which were positive for TOP2A (green line) had a better survival than the cases which were negative (blue line).

B) Scatter plot of transcript levels of TOP2a in different grades of astrocytoma.

Log 2-transformed gene expression ratios obtained from RT-qPCR analysis of indicated samples are plotted for TOP2A. Horizontal line in each group designates the median value.

FIG. 2

Scatter plots of transcript levels of topoisomerase family members in different grades of astrocytoma.

Log 2-transformed gene expression ratios obtained from RT-qPCR analysis of indicated samples are plotted for TOP1

(A), TOP2B (B), TOP3A (C), TOP3B (D) and TOPORS (E). Horizontal line in each group designates the median value.

FIG. 3

A) Etoposide inhibits plasmid relaxation activity by TOP2a.

A plasmid relaxation assay by TOP2A enzyme was carried out in the absence of etoposide (lane 2) or increasing concentrations of etoposide (lane 3-5) or ethanol (vehicle control) (lane 6).

B) Temozolomide inhibits plasmid relaxation activity by TOP2A

A plasmid relaxation activity by TOP2A enzyme was carried out in the absence of temozolomide (lane 2) or increasing concentrations of temozolomide (lane 3-4) or DMSO (vehicle control) (lane 5).

C) siRNA knockdown of TOP2A.

Cell lysates were prepared from control (cyclophilin) and TOP2A siRNA treated after 48 hrs and equal amount of protein was subjected to immunoblotting with the indicated antibodies.

D) Downregulation of TOP2A renders glioma cells resistant to etoposide chemotherapy.

U251 cells transfected with either cyclophilin (red) or TOP2A (blue) siRNA were treated with indicated concentrations of etoposide and the proportion of live cells was quantified by MTT assay after 48 hrs. At test for difference in the % viability of the control and TOP2A siRNA treated cells was estimated and the p values are shown: 2, 4, 8 and 16 µg/mL; p=0.0297, 0.0336, <0.0001 and 0.042 respectively.

E) Downregulation of TOP2A renders glioma cells resistant to temozolomide chemotherapy.

The experiment was carried out as in "D" but the cells were treated with temozolomide. At test for difference in the % viability of the control and TOP2A siRNA treated cells was estimated and the p values are shown: 250, 500, 1000 and 2000 µM; p=0.0668, 0.0097, 0.0687 and 0.0134 respectively.

FIG. 4

Transcript levels of topoisomerase family members in glioma cell lines.

Log 2-transformed gene expression ratios obtained from real-time reverse transcription quantitative PCR analysis of RNA derived from glioma cell lines (light pink bars, left to right order of cell lines: LN18, LN229, U138, U251, U343, U373, U87) are plotted for TOP1, TOP2A, TOP2B, TOP3A, TOP3B and TOPORS. Each bar represents a data derived from one sample. In each sample, fold change in gene expression is calculated over its mean expression in normal brain samples (dark pink bars).

TABLE 1A

Statistical Analysis of Transcript Levels TOP2A, TOP2B, TOP3A and TOPORS in Different Grades of Glioma Bonferroni post-hoc analysis test showing a significant P-value; α: Normal Vs DA; β: Normal Vs AA; γ: Normal Vs GBM; δ: DA Vs AA; ε: DA Vs GBM; η: AA Vs GBM; the number of samples used in each group is indicated by 'n'.

TABLE 1B

Individual Group Differences in the Labeling Index I (IHC) of TOP2A

Values in parenthesis are median; Bonferroni adjusted post-hoc test showing a significant P-value in bold; ε=Normal Vs GBM, £=DA Vs GBM, ‡=AA Vs GBM.

DETAILED DESCRIPTION

The present invention provides a TOP2A inhibition by temozolomide useful for predicting glioblastoma patient's survival. The present invention relates to a method of identifying prognostic marker for GBM in patients receiving temozolomide chemotherapy.

Accordingly, the present invention provides an in vitro method of determining prognosis of glioblastoma, wherein the said method comprises determining the level of expression of the gene TOP2A in a test sample and in a control sample, wherein a higher level of expression of TOP2A in the test sample, as compared to the control sample, indicates good prognosis of glioblastoma.

In one embodiment of the present invention, the test sample is brain tumor tissue cells obtained from human subjects who underwent surgery and ready to receive radiotherapy with concomitant and cyclical adjuvant temozolomide therapy.

In another embodiment of the present invention, determining the level of expression of the said gene comprises determining the levels of the mRNA transcripts of the said genes by employing an oligonucleotide in nucleic acid based detection methods such as, in situ hybridization or RT-PCR analysis etc or optionally determining the levels of the respective proteins of the said genes by employing an antibody in protein based detection methods such as, immunohistochemistry, ELISA or Western blot analysis etc.

In still another embodiment of the present invention, a method of detecting cytotoxicity of temozolomide in glioblastoma patients wherein cells with low concentration of TOP2A protein is less sensitive to temozolomide than cells containing high concentration of TOP2A.

In yet another embodiment of the present invention, A kit for determining the prognosis of glioblastoma in a human subject undergoing temozolomide therapy, wherein the said kit comprises:
  a) Reagent capable of specifically detecting the level of expression of the gene TOP2A in receiving radiotherapy with concomitant and cyclical adjuvant temozolomide therapy.
  b) Instructions for using said kit for determining the prognosis of glioblastoma in said human subject receiving radiotherapy with concomitant and cyclical adjuvant temozolomide therapy.

In still another embodiment of the present invention, the reagent in the kit comprises a nucleic acid probe complementary to mRNA of the said gene.

In still another embodiment of the present invention, the reagent in the kit comprises an antibody that specifically binds to protein encoded by the said gene.

A prospective study is performed where patients are selected with standard inclusion/exclusion criteria and subjected to uniform treatment protocol, which included maximal safe resection of the tumor followed by radiotherapy with concomitant and cyclical adjuvant temozolomide therapy. The patients' survival data was correlated with tumor gene expression profile for identifying genes whose expression signature could predict survival. The observations regarding influence of high topoisomerase II alpha (TOP2A) transcripts in GBM on patient survival is reported herewith. It is further demonstrated by functional studies that temozolomide inhibits TOP2A activity in vitro and silencing of TOP2A in glioma cells renderes them temozolomide resistant. An assessment of TOP2A and other isoforms of topoisomerase across the grades of astrocytoma were also performed to elucidate their role in glioma.

EXAMPLES

The following examples are given by way of illustration of the present invention and therefore should not be construed to limit the scope of the present invention.

Example 1

Collection of Tumor Samples

Tumor samples were collected from patients who were operated at Sri Sathya Sai Institute of Higher Medical Sciences (SSSIHMS) and National Institute of Mental Health and Neurosciences (NIMHANS), Bangalore, India. Normal brain tissue (anterior temporal lobe) obtained during surgery for intractable epilepsy was used as control samples. The study has been scrutinized and approved by the ethics committee of the two clinical centers and patient consent was obtained prior to initiation of the study as per the IEC guidelines and approval.

Example 2

Cell Lines, siRNA and Transfection

U373, U138, LN18, LN229, U343, U87, K562, U251 and SVG cells were cultured in DMEM respectively with 10% Fetal bovine serum, penicillin and streptomycin at 37° C. in a humidified atmosphere with 5% $CO_2$. The human TOP2A and cyclophilin siRNA duplexes were designed and chemically synthesized by Dharmacon Research (Lafayette, Colo.). The SMARTpool siRNA is a mixture of four different siRNA duplexes targeting distinct coding region sequences of TOP2A (Genbank™ accession number NM_001067). The siRNA duplexes were dissolved in the 1× universal RNA oligo buffer (20 mM KCl, 6 mM HEPES-KOH (pH 7.5), 0.2 mM $MgCl_2$). SiRNA transfections (200 nM) were carried out using Dharmafect (Dharmacon Research) as per the manufacturer's instructions.

Example 3

Cell Viability Assay

For chemosensitivity assays, 24 hours after plating, the cells were treated with the cytotoxic drugs and incubated at 37° C., 5% $CO_2$ for 45 hours. At this point, MIT (20 µl of 5 mg/mL) was added to the cells. Three hours after MTT addition, the formazan crystals were dissolved in DMSO (200 µl) and measured as absorbance at 550 nm. The absorbance by the control cells was considered to be 100% and all samples were normalized to the control cells. All assays were carried out in triplicates.

Example 4

RNA Isolation and RT-qPCR

Total RNA was extracted from the frozen tissue by using TRI Reagent (Sigma, USA). The RNA samples were quantified by measuring the absorbance using a spectrophotometer and visualized on a MOPS-Formaldehyde gel for quality assurance. The relative quantitation of expression levels of selected genes was carried out using two step strategy: in the first step, cDNA was generated from RNA derived from different tissue samples using cDNA Archive kit (ABI PRISM); subsequently real-time quantitative PCR was carried out in ABI PRISM 7900 (Applied Biosystems) sequence detection system with the cDNA as template using gene specific primer sets and Dynamo kit containing SYBR green dye (Finnzyme, Finland). All measurements were made in triplicate. The genes GARS (glycyl-tRNA synthetase), AGPAT1 (1-acylglycerol-3-phosphate O-acyltransferase 1), ATP5G1 (ATP synthase, H+ transporting, mitochondrial F0 complex, subunit C1 (subunit 9)) and RPL35A (ribosomal protein L35a) were used as internal controls as their expression levels were found to be unaltered in the array experiments. Normal brain tissue samples from epilepsy patients were used as reference. Delta delta CT method was used for the calculation of ratios. Sequences of RT-PCR primers and conditions used will be provided on request. Each dot in FIGS. 1B and 2 A, B, C, D and E represents the median transcript levels from one sample after normalization with the internal reference genes. RNA expression levels (Log 2 ratios) of all groups (Normal, DA, AA and GBM) were tested for normal distribution and they were found to be not normally distributed. The results were expressed in the form of mean log 2 ratio±SD. The comparison between the groups was performed using Kruskal-Wallis one-way analysis of Variance, and further comparison within subgroups was performed with Bonferroni adjusted post-hoc analysis using SPSS version 16.0 software.

Example 5

Western Blotting

Protein lysates from cell lines were prepared in RIPA buffer and equal amount of total protein was used for immunoblotting after quantitation by Bradford's reagent. The following antibodies were used in this study—TOP2A (Dakocytomation; Cat# M7186; 1:250) and Actin (Sigma; Cat # A3854; 1:25,000).

Example 6

TOP2A Enzyme Assay

TOP2A activity was measured in vitro using a plasmid relaxation assay. Briefly, relaxation assays contained plasmid DNA (pBR322; 200 ng per reaction) and 2 units of TOP2A (Topgen Cat#200H-2) in a final volume of 30 µl in topoisomerase II reaction buffer (50 mM Tris-Cl at pH 8.0, 150 mM KCl, 10 mM $MgCl_2$, 5 mM ATP, 0.5 mM DTT, 30 µg/ml BSA). The reactions were incubated at 37° C. for 30 min, and terminated by the addition of 2.5 µl loading dye (30% glycerol and 0.25% bromophenol blue). The samples were analyzed on 1% native agarose gel (without any intercalator). Gels were stained with ethidium bromide for 10-15 min. To determine the effect of the etoposide or temozolomide, specific amounts were added in the reaction mixture.

Example 7

Immunohistochemistry (IHC)

Paraffin sections (4 μm) from the tumor tissue and control samples were collected on silane coated slides and protein expression of TOP2A was assessed by immunohistochemistry (IHC) on 127 samples (16 DA, 21 AA, 77 GBM and 13 control samples). The heat-induced antigen retrieval of the deparaffinized sections was performed in a microwave oven for 30-35 minutes at 600 W in citrate buffer (10 mM, pH 6.0). After the initial processing steps, sections were incubated overnight with TOP2A (Dakocytomation; Cat# M7186 at 1:60 dilution) primary antibody overnight at room temperature. This was followed by incubation with the supersensitive non-biotin HRP detection system (QD440-XAK, Biogenex, USA). 3,3'-Diaminobenzidine (Sigma-Aldrich, St. Louis, U.S.A) was used as the chromogenic substrate. Tumors that showed markedly increased mRNA levels of TOP2A served as positive controls. A negative control slide in which the primary antibody is excluded was incorporated with each batch of staining. Both nuclear and cytoplasmic staining was noted. The nuclear and cytoplasmic immunohistochemical staining were scored semi-quantitatively on a three-point scale of 0-2, where 0=no staining, 1+=mild staining, and 2+=strong staining within the tumor core. Only 2+ nuclear and cytoplasmic positivity were considered for analysis. The immunopositivity was assessed in more than 1000 cells from each tumor specimen. The labeling index (LI) was expressed as percentage of cells that showed 2+ staining among the total number of cells counted.

Example 8

Statistical Analyses for IHC Data

All continuous variables were tested for normal distribution and they were found to be non-normal. In order to determine the grade specific expression pattern, a non-parametric test, Kruskal-Wallis One-Way Analysis of Variance on Ranks, was performed on the data assessed by IHC. Significance in the differences between the means of all of the four groups was determined by one way ANOVA followed by Bonferroni adjusted post hoc test for multiple comparisons. The results were expressed in the form of mean LI±SD. All analyses were performed using SPSS ver. 15.0.

Example 9

Tumor Samples

Tumor samples were collected from patients who were operated at Sri Sathya Sai Institute of Higher Medical Sciences (SSIHMS) and National Institute of Mental Health and Neurosciences (NIMHANS), Bangalore, India. Normal brain tissue (anterior temporal lobe) obtained during surgery for intractable epilepsy was used as control samples. The study has been scrutinized and approved by the ethics committee of the two clinical centers and patient consent was obtained prior to initiation of the study as per the IEC guidelines and approval. Tissues were bisected and one half was snap-frozen in liquid nitrogen and stored at −80° C. until RNA isolation. The other half was fixed in formalin and processed for paraffin sections. These were used for histopathological grading of astrocytomas and immunohistochemistry. A total of 276 samples which included 172 glioblastomas (GBMs), 54 anaplastic astrocytomas, grade III (AAs), 30 diffuse astrocytomas, grade II (DAs) and 20 normal controls have been used in this study. Out of 172 GBM samples, 102 were derived from prospectively selected cohort of GBM patients who underwent standardized treatment protocol (see later for details). The protein expression of TOP2A was analyzed on tumor tissue sections by IHC on 127 samples.

Example 10

Survival Correlation with TOP2A mRNA Levels

Newly diagnosed glioblastoma patients (n=102) who underwent surgery in the two clinical centers (NIMHANS/SSIHMS) were prospectively included. Approval by the ethics committee and patient consent were obtained prior to initiation of the study. The patients were recruited based on the following inclusion criteria: 1) Adult patients (age between 18 to 65 years) with a supratentorial lobar tumor 2) Patients who underwent maximal safe resection of the tumor with minimal residue noted on post operative MRI scan 3) Patients with post operative Karnofsky's Performance Score (KPS)≥70.

All patients underwent maximal safe resection of the tumor. All patients underwent uniform adjuvant therapy consisting of radiotherapy, administered with a total dose of 59.4 Gy, given in 33 fractions, along with concomitant chemotherapy with temozolamide, administered at the dose of 100 mg/day which was continued daily for 45 days. Subsequently, five cycles of cyclical chemotherapy with temozolamide at the dose of 150 mg/sq. m body surface area for 5 days every 28 days was administered. The patients were followed up clinically and with MR imaging. The maximum follow up period was 34 months.

Results and Discussion

High TOP2A Level is Good Prognostic Indicator in GBM Patients

A cohort of 102 patients of GBM were prospectively recruited and managed by standard treatment protocol (as explained in methods). The median overall survival for this group was found to be 16 months (Kaplan Meier analysis). In this cohort, as expected, age was an important predictor of poor outcome as noted by Cox regression analysis (p=0.037; HR=1.023; B=0.022). Interestingly, it was noted that TOP2A mRNA expression significantly correlated with prognosis in GBM patients; higher TOP2A transcript level predicted better prognosis (p=0.043; HR=0.889; B=−0.117; Cox regression analysis). The effect of TOP2A transcript level and age on survival was further evaluated by Cox proportional hazard model to elicit the independent effect of TOP2A on survival. It was noted that both age (p=0.033; HR=1.023; B=0.023) and TOP2A transcript level (p=0.035; HR=0.888; B=−0.119) were significant predictors by multivariate analysis. On further analysis, the TOP2A mRNA expression was dichotomized to elucidate a cutoff in predicting prognosis. It is reported that patients with TOP2A mRNA levels<9.25 log 2 ratio had a significantly poorer prognosis, when compared to those with mRNA levels≥9.25 log 2 ratio (median survival of 13 months vs 22 months respectively; p=0.048) (FIG. 1A).

Regulation of TOP2A and Other Topoisomerase Family Members in Astrocytoma

Figure 2:
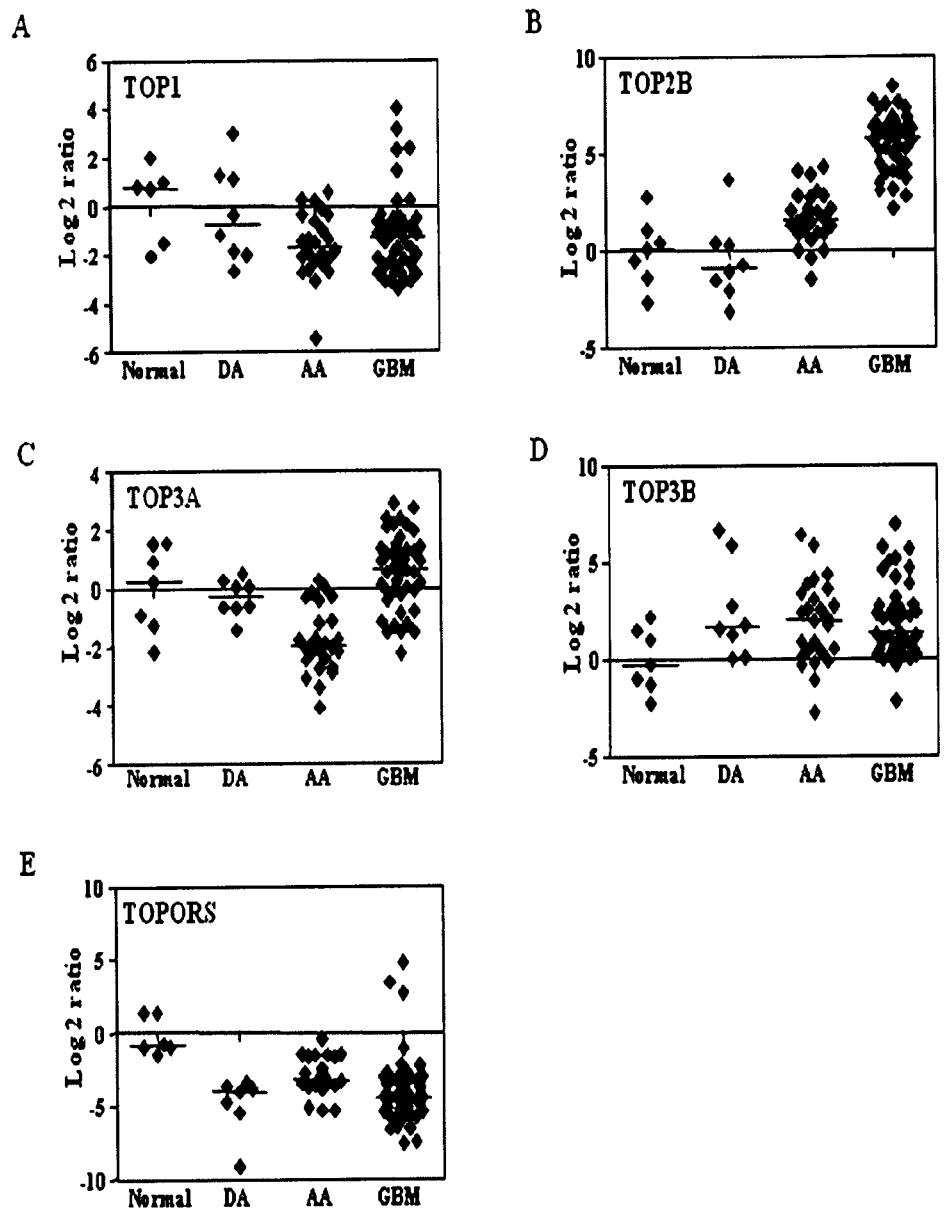
Figure 4:
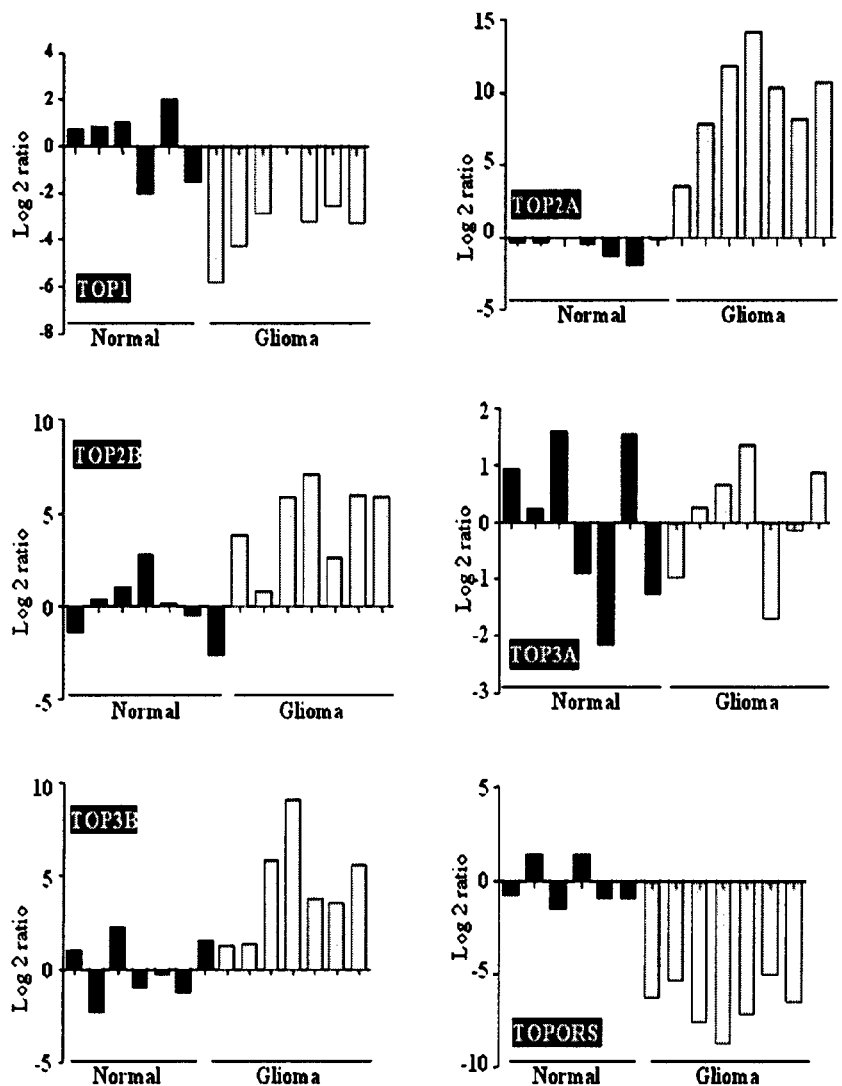

Further investigations related to the regulation of expression of TOP2A and other members of the topoisomerase family in glioblastoma and other lower grades of astrocytoma was done. It is hereby reported that the transcript levels of TOP2A is significantly upregulated to very high levels in GBMs as compared to DA, AA and normal brain samples (FIG. 1B; Table 1A). A significant increased expression of TOP2A protein (nuclear) was observed in glioblastoma in comparison to the other grades while, there was a decrease in its cytoplasmic expression with ascending grades of malignancy in astrocytoma (Table 1B). Similarly, TOP2B transcript level was also found upregulated in GBMs as compared to DA, AA and normal brain samples (FIG. 2B; Table 1A). In addition, TOP3A transcript levels were also found upregulated in GBM as compared to DA and AA (FIG. 2C; Table 1A). Unlike these genes, the transcript levels of TOPORS were found significantly downregulated in malignant astrocytomas (AA and GBM) as compared to normal brain samples (FIG. 2E; Table 1A). The other members of topoisomerase family, TOP1 and TOP3B did not show differential regulation across different grades of glioma (FIGS. 2 A and D). In good correlation, a similar regulation of topoisomerase family genes in established glioma derived cell lines was found as well (FIG. 4).

Temozolomide Inhibits TOP2A Activity

Figure 3:
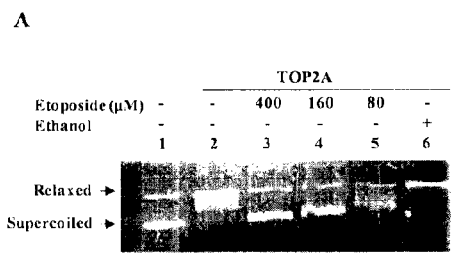
Figure 3:
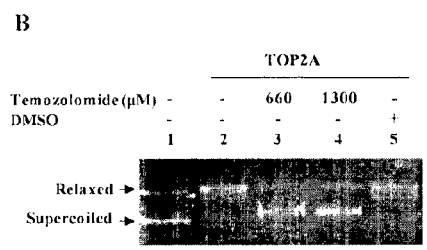
Figure 3:
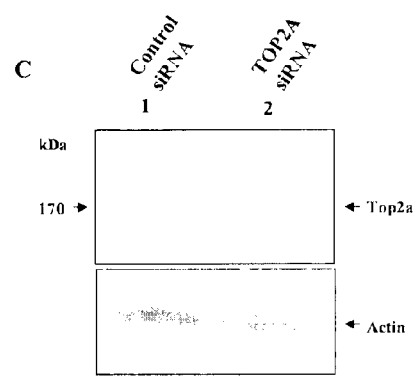
Figure 3:
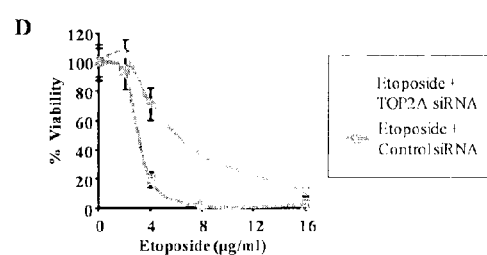
Figure 3:
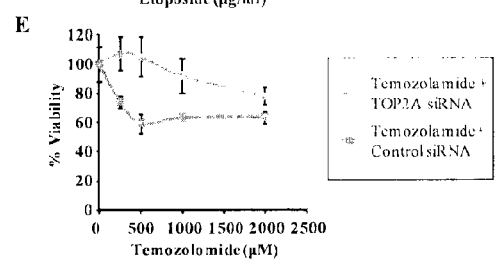

Cancer cells with high TOP2A levels have been shown to be more sensitive to TOP2A inhibitors like etoposide without any effect on cell growth (Hao et al., 2000; Asano et al., 1996; Zhou et al., 2001). Since our results indicate that GBM patients with high levels of tumor TOP2A respond better to temozolomide chemotherapy, it is hypothesized that temozolomide could be a TOP2A inhibitor. To test this possibility, we carried out TOP2A enzyme assay in which the ability of TOP2A (170 kDa) enzyme to relax the super coiled plasmid DNA in the presence of temozolomide was evaluated. The TOP2A enzyme relaxed the supercoiled plasmid DNA very efficiently (FIG. 3A compare lane 2 with 1). The addition of etoposide, which is a known TOP2A inhibitor, to this reaction inhibited the TOP2A relaxation activity very efficiently in a concentration dependent manner (FIG. 3A compare lanes 5, 4 and 3 with 2). Interestingly, the addition of temozolomide also inhibited TOP2A relaxation activity efficiently (FIG. 3B compare lanes 3 and 4 with 2). Thus these results indicate that temozolomide is a TOP2A inhibitor.

TOP2A Knock-Down Confers Chemo Resistance in Glioma Cells

As our results show that temozolomide inhibits TOP2A enzyme activity and GBM patients with high tumor TOP2A responded better to temozolomide chemotherapy, it is hypothesized that down regulation of TOP2A will confer

TABLE 1A

Statistical analysis of transcript levels TOP2A, TOP2B, TOP3A and TOPORS in different grades of glioma

| Biomarker | Normal | DA (Grade II) | AA (Grade III) | GBM (Grade IV) | *Bonferroni adjusted post-hoc P-value | Kruskal-Wallis test $\chi^2$ | P-value |
|---|---|---|---|---|---|---|---|
| TOP2A | 0.0005 ± 1.2871 (n = 20) | 5.1479 ± 1.7693 (n = 28) | 5.7798 ± 1.9201 (n = 50) | 7.9436 ± 2.2517 (n = 156) | $\alpha$ = <0.0001<br>$\beta$ = <0.0001<br>$\gamma$ = <0.0001<br>$\epsilon$ = <0.0001<br>$\eta$ = <0.0001 | 107.4229 | <0.0001 |
| TOP2B | 1.4999 × 10$^{-8}$ ± 1.7343 (n = 7) | −0.5126 ± 2.0461 (n = 8) | 1.6853 ± 1.3852 (n = 26) | 5.6108 ± 1.4358 (n = 44) | $\gamma$ = <0.0001<br>$\delta$ = 0.0166<br>$\epsilon$ = <0.0001<br>$\eta$ = <0.0001 | 60.7461 | <0.0001 |
| TOP3A | 7.1485 × 10$^{-7}$ ± 1.4654 (n = 7) | −0.2967 ± 0.6329 (n = 8) | −1.7894 ± 1.1239 (n = 26) | 0.5702 ± 1.2842 (n = 44) | $\beta$ = 0.0394<br>$\delta$ = 0.0070<br>$\eta$ = <0.0001 | 36.7250 | <0.0001 |
| TOPORS | −0.2286 ± 1.2823 (n = 6) | −3.5518 ± 4.2444 (n = 7) | −3.9898 ± 3.6838 (n = 23) | −3.8809 ± 2.4994 (n = 44) | $\beta$ = <0.0001<br>$\gamma$ = 0.0010 | 15.5610 | 0.0013 |

*Bonferroni post-hoc analysis test showing a significant P-value; α: Normal Vs DA; β: Normal Vs AA; γ: Normal Vs GBM; δ: DA Vs AA; ε: DA Vs GBM; η: AA Vs GBM; the number of samples used in each group is indicated by 'n'

TABLE 1B

Individual group differences in the labeling index I (IHC) of TOP2A

| Biomarkers | Normal (n = 13) Mean ± SD | DA(Grade II) (n = 16) Mean ± SD | AA (Grade III) (n = 21) Mean ± SD | GBM (Grade IV) (n = 77) Mean ± SD | Kruskal Wallis test: $\chi^2$; P value | Post-hoc P value* |
|---|---|---|---|---|---|---|
| TOP2A2+ NUCLEAR | 0.0000 ± 0.0000 (0.0000) | 8.4375 ± 8.107353 (5.0000) | 6.666667 ± 8.416254 (5.0000) | 17.07792 ± 10.52412 (20.000) | 42.313; <0.0001 | $\epsilon$ < 0.0001<br>£ = 0.0115<br>‡ = 0.0009 |
| TOP2A 2+ CYTO | 0.0000 ± 0.0000 (0.0000) | 11.25 ± 7.637626 (10.0000) | 9.761905 ± 9.679384 (5.0000) | 4.025974 ± 7.391272 (0.000) | 32.322; <0.0001 | $\epsilon$ = 0.2064<br>£ = 0.0001<br>‡ = 0.0083 |

Values in parenthesis are median;

*Bonferroni adjusted post-hoc test showing a significant P-value in bold; $\epsilon$ = Normal Vs GBM, £ = DA Vs GBM, ‡ = AA Vs GBM.

glioma cells resistance to temozolomide. TOP2A-specific siRNA transfection reduced (61%) the TOP2A protein levels efficiently in U251 glioma cells (FIG. 3C). U251 cells transfected with TOP2A-specific siRNA are found to be significantly resistant to temozolomide treatment in comparison to cyclophilin siRNA transfection (FIG. 3E). As shown by others, etoposide inhibited TOP2A siRNA transfected cells less efficiently than cyclophilin siRNA transfected cells (FIG. 3D). Thus these results suggest that Temozolomide acts through TOP2A pathway by probably causing its inhibition and high TOP2A levels provide sensitivity to temozolomide chemotherapy.

Predicting the benefit for a given therapeutic modality remains a challenging task in cancer biology and is very important for individualized anticancer therapy. Variety of attempts like radiotherapy schedule and dose and addition of nitrosourea-based chemotherapy to improve the prognosis of GBM patients yielded only minimal success (Stewart, 2002). It is now established that temozolomide increases the survival of GBM patients when combined with radiotherapy as concomitant and cyclical adjuvant therapy (Hart et al., 2008). Interestingly, GBM patients with methylated MGMT promoter gene in tumor had better survival (Stupp et al., 2009). Temozolomide cytotoxicity is mediated mainly through methylation of the 06-position of guanine. Since this DNA damage is rapidly repaired by MGMT, epigenetic silencing of MGMT has been proposed as a predictive factor for benefit from chemotherapy with alkylating agents like temozolomide. Thus the MGMT-promoter methylation appears to be the first predictive biomarker in GBM tumors that allows selection of patients who will benefit most from treatment with temozolomide and radiotherapy (Stupp et al., 2009). From these observations, the use of molecular markers to predict tumor response to chemotherapy appears to be very important.

On evaluation of prognostic significance of expression of genes in GBM patients treated with concomitant and adjuvant temozolomide chemotherapy, it was found that TOP2A mRNA expression significantly correlated with prognosis in GBM patients with higher TOP2A transcript level predicting better prognosis. In particular, GBM patients with tumor TOP2A transcript levels≥9.25 log 2 ratio had better survival than those patients with tumor TOP2A transcript levels less than 9.25 log 2 ratio. It was our interest to study why tumors with high TOP2A levels responded better to temozolomide therapy. TOP2A encodes a DNA topoisomerase enzyme that controls the topological states of the DNA during various important processes of DNA metabolism including transcription, recombination, replication and chromosome segregation during cell division (Järvinen and Liu, 2003). The eukaryotic topoII is a homodimeric enzyme that exists in two isoforms in human cells: the major, 170-kd topoIIα and 180-kd IIβ (Wang, 1996). While these two enzymes share considerable homology (72%), they are products of different genes located in chromosomes 17q21 and 3p (Järvinen and Liu, 2003). Whereas TOP2A carries out the vital functions during the segregation and condensation of the replicated chromosomes, the exact function of TOP2B is still largely unknown (Isaacs et al., 1998; Yang et al., 2000). It is noted that the mRNA levels of TOP2A was significantly higher in GBM as compared to AA and DA, which was also reflected in the nuclear protein expression by IHC. Previous studies have demonstrated a similar variation by IHC only in a small number of cases. The significance of such variation needs further evaluation. (Holden and Townsend, 1999; Faria et al., 2006). Interestingly, the relatively high TOP2A levels seen in grade II/III, may suggest that similar correlation between TOP2A mRNA and patient survival, which although requires further evaluation It is reported that few other members of topoisomerase family—TOP2B and TOP3A are upregulated in glioblastoma, the significance of which is not clear at present. Interestingly we found TOPORS downregulated in malignant glioma which can explained by the report that TOPORS is a binding protein and coactivator of p53 with the resultant role in mediating p53-dependent cellular responses induced by DNA damage (Lin et al., 2005)

Elevated levels of TOP2A transcript and protein often correlating with increased cell proliferation is documented in many cancers including breast cancer, cervical cancer, small cell lung cancer, gastric cancer, stomach and colon cancer (Järvinen and Liu, 2003). In glioma, high levels of TOP2A mRNA has been noted in GBMs in comparison to grade II and III astrocytomas and is also correlated with tumor TOP2A protein levels (Oda et al., 2005). TOP2A gene is located very close to HER-2 oncogene at the chromosome 17q12-q21 and is amplified or deleted in almost 90% of HER-2 amplified primary breast cancers. More interestingly, the amplification or deletion of TOP2A may account for both relative chemosensitivity and resistance to antharacycline therapy (Järvinen and Liu, 2003). Further, in vitro studies using different experimental methods have previously proved that the sensitivity to the TOP2A-inhibitors is dependent on the expression level of TOP2A in cancer cells—cells with a low concentration of TOP2A protein are less sensitive to TOP2-inhibiting drugs than cells containing a high concentration of TOP2A (Asano et al., 1996; Järvinen et al., 2000; Gudkov et al., 1993; Asano et al., 1996; Vassetzky et al., 1996; Withoff et al., 1996).

Based on initial finding that GBM patients with high tumor TOP2A transcript levels had better survival to temozolomide chemotherapy, it is hypothesized that temozolomide may also act by influencing TOP2A enzyme activity. Indeed, we were able to demonstrate that temozolomide is an inhibitor of TOP2A in vitro. Further, we propose that the reason for better response of GBM tumors with high TOP2A levels to temozolomide therapy could be that tumors with high TOP2A levels are more dependent on TOP2A for their survival and are inhibited very efficiently by temozolomide through its TOP2A inhibitory activity. The present invention reports that TOP2A levels of glioma cells determine their sensitivity to temozolomide with cells becoming resistant to temozolomide upon downregulation of TOP2A. Thus the present study demonstrates tumor TOP2A transcript levels as a predictor of response to temozolomide chemotherapy.

ADVANTAGES

The advantages of the present invention are:
1. It provides a useful prognostic indicator TOP2A for the GBM patients receiving radiotherapy with concomitant and cyclical adjuvant temozolomide therapy.
2. Hence, it is possible to decide the most appropriate therapy.

The invention claimed is:
1. A method of radiotherapy with concomitant and cyclical adjuvant temozolomide therapy for a human individual with glioblastoma brain tumors comprising:
   determining an expression level for topoisomerase II alpha (TOP2A) in a sample of brain tumor tissue cells from a human subject surgically treated for glioblastoma;
   obtaining a reference expression level for TOP2A in a control sample of known normal brain tissue cells;

calculating a ratio by comparing the expression level for TOP2A of the sample of brain tumor tissue cells with the reference expression level for TOP2A of the control sample of known normal brain tissue cells;
based upon a determination that the ratio of the sample expression level of TOP2A to the reference expression level of TOP2A is ≥9.25 log 2 ratio, determining that the individual has an increased chance of survival post glioblastoma brain tumor surgery; and
based upon the ratio of the sample expression level of TOP2A to the reference expression level of TOP2A being ≥9.25 log 2 ratio, treating the individual with a radiotherapy with concomitant and cyclical adjuvant temozolomide therapy post-surgery, wherein the temozolomide acts as a TOP2A inhibitor as a result of the treating.

2. The method of claim 1, further comprising based upon the ratio of the sample expression level of TOP2A to the reference expression level of TOP2A being <9.25 log 2 ratio, not treating the individual with a radiotherapy with concomitant and cyclical adjuvant temozolomide therapy post-surgery.

3. A method of radiotherapy with concomitant and cyclical adjuvant temozolomide therapy for a human individual with glioblastoma brain tumors comprising:
determining an expression level for TOP2A in a sample of brain tumor tissue cells from a human subject surgically treated for glioblastoma; wherein the TOP2A expression level is determined by a real-time reverse transcription quantitative polymerase chain reaction comprising a nucleic acid probe complementary to an mRNA of a TOP2A gene or an antibody that binds to a protein encoded by the TOP2A gene;
obtaining a reference expression level for TOP2A in a control sample of known normal brain tissue cells;
calculating a ratio by comparing the expression level for TOP2A of the sample of brain tumor tissue cells with the reference expression level for TOP2A of the control sample of known normal brain tissue cells;
based upon a determination that the ratio of the sample expression level of TOP2A to the reference expression level of TOP2A is ≥9.25 log 2 ratio, determining that the individual has an increased chance of survival post glioblastoma brain tumor surgery; and
based upon the ratio of the sample expression level of TOP2A to the reference expression level of TOP2A being ≥9.25 log 2 ratio, treating the individual with a radiotherapy with concomitant and cyclical adjuvant temozolomide therapy post-surgery, wherein the temozolomide acts as a TOP2A inhibitor as a result of the treating; and
based upon the ratio of the sample expression level of TOP2A to the reference expression level of TOP2A being <9.25 log 2 ratio, not treating the individual with a radiotherapy with concomitant and cyclical adjuvant temozolomide therapy post-surgery.

* * * * *